United States Patent [19]

Telfer et al.

[11] Patent Number: 4,482,541

[45] Date of Patent: Nov. 13, 1984

[54] WATER SOLUBLE GLASS ARTICLES, THEIR MANUFACTURE, AND THEIR USE IN THE TREATMENT OF RUMINANT ANIMALS

[75] Inventors: Stewart B. Telfer; George Zervas; Peter Knott, all of Leeds, England

[73] Assignee: University of Leeds Industrial Services Limited, England

[21] Appl. No.: 468,911

[22] Filed: Feb. 23, 1983

[30] Foreign Application Priority Data

Feb. 23, 1982 [GB] United Kingdom ............... 8205233

[51] Int. Cl.³ .............................................. A61K 33/42
[52] U.S. Cl. .................................... 424/128; 424/131; 424/140; 424/144; 424/145; 424/150; 424/154; 424/163
[58] Field of Search ............... 424/357, 128, 131, 140, 424/144, 145, 150, 154, 163

[56] References Cited

U.S. PATENT DOCUMENTS 4,349,025 9/1982 Drake ...................................... 424/9
4,350,675 9/1982 Drake ...................................... 424/9

Primary Examiner—Sam Rosen
Attorney, Agent, or Firm—Sughrue, Mion, Zinn, Macpeak & Seas

[57] ABSTRACT

A water soluble glass article suitable for treating a diet deficiency in a ruminant animal. Animals are treated by lodging in the reticulo rumen an article containing
(a) $P_2O_5$
(b) $R_2O$ where R is chosen from Na, K and Li
(c) at least one other glass forming or modifying material, usually CaO, MgO or $Al_2O_3$
(d) at least one deficiency-rectifying element selected from Cu, Se, Co, Zn, I, Mn and Mg.

In the composition the sum of $P_2O_5$ and $R_2O$ is not less than 56 mol %, and not more than 76 mol % if CuO and/or ZnO are present or not more than 92 mol % if CuO and/or ZnO are absent and one or more of CoO, SeO and I is present. If CuO and/or ZnO is present then the amount of each of $P_2O_5$ and $R_2O$ (preferably present in substantially equimolar amounts) does not exceed 45 mol %.

The composition is such that when the article is present in the reticulo rumen the article has a release rate of not more than 25 mg per square centimeter of article surface area per day, so making possible articles which can be administered to the animal to release the required element or elements over periods up to one year or more.

27 Claims, No Drawings

WATER SOLUBLE GLASS ARTICLES, THEIR MANUFACTURE, AND THEIR USE IN THE TREATMENT OF RUMINANT ANIMALS

This invention relates to water soluble glass articles, their manufacture and their use in the treatment of ruminant animals to remedy deficiencies in the animals of elements that may be lacking in the available diet. The treatment is carried out by the administration of a water soluble glass article to lodge in the reticulo rumen of the animal to be treated. The term reticulo rumen is used herein to mean the reticulum plus the rumen. Water soluble glasses are becoming well known in the art. For example GB Pat. No. 2057420A describes a water soluble glass incorporating materials that will release a trace element or therapeutic element as the glass dissolves and exemplifies use of such compositions in human and animal therapy and preventive medicine. For example, the glass compositions described therein can be made into a monolithic block of animal lick or can be ground into a particulate form in which it can be fed as a dietary supplement to farm animals.

In the particular context of preventing or curing trace element deficiencies in animals, proposals have also been made that animals should be implanted subcutaneously with a soluble glass containing the required trace elements, those elements being released into the blood stream of the animal as the implant dissolves. Such implants, apart from the difficulty of administering them, seem to create unwanted side effects in certain instances, and especially can involve problems when copper has been administered as the trace element. However, even then they may be thought preferable to diet supplementation which may be even more difficult to accomplish, particularly when extensive rather than intensive farming is being practised.

The present invention has for its object the provision of a water soluble glass that can be formed into an article for insertion into the reticulo rumen of a ruminant animal to provide that animal with one or more deficiency-rectifying elements released into the animal's life system over an extended period of time. Quite apart from this particular use the novel glasses to be described may also be useful in different physical form for the treatment of certain conditions in humans, for the treatment of ruminant animals other than by administration of an article to lodge in the reticulo rumen and for the treatment of other animals.

According to the present invention we provide a water soluble glass article in a form suitable for administration to a ruminant animal to lodge in the reticulo rumen of the animal, the article containing:

(a) $P_2O_5$
(b) $R_2O$ where R is chosen from Na, K and Li
(c) at least one other glass forming or modifying material
(d) at least one deficiency-rectifying element combined in the glass, said element being selected from Cu, Se, Co, Zn, I, Mn and Mg in which:

when CuO is present in the glass the content of each of $P_2O_5$ and $R_2O$ does not exceed 45 mol%;

when one or more of CuO and ZnO is present in the glass the sum of the quantities of $P_2O_5$ and $R_2O$ is in the range of 56–76 mol%;

when CuO and ZnO are absent and one or more of MgO, CoO, SeO and I is present in the glass the sum of the quantities of $P_2O_5$ and $R_2O$ is in the range of 56–92 mol%;

and the composition being such that when the glass article is present in the reticulo rumen of the animal the article has a release rate of not more than 25 mg per square centimeter of article surface area per day.

The article is desirably of such a size that it can be administered orally to a ruminant animal to lodge in the reticulo rumen of the animal. When so lodged it is found that the article will dissolve over a period of at least some six weeks to release the deficiency-rectifying elements into the animal's life system. By using the lower range of release rates contemplated by the invention, treatment periods well in excess of six weeks can be achieved, thus a release rate of up to 8 mg/cm$^2$/day will provide treatment for about one year.

Prior proposals such as GB Pat. No. 2057420A are primarily concerned with using glasses in a particulate form and in such cases the surface area exposed within the animal is much higher than is the case with a solid article of the volume necessary to provide sustained release for periods from 6 weeks to a year or even longer. Thus, in the prior art glass, the solubility is substantially lower than that achieved with the present invention. No glasses are taught with a $P_2O_5$ content less than 50 mol% and the alkali metal oxide content according to the corresponding U.S. Pat. No. 4,350,675 must not exceed 20 mol%. Such glasses would be wholly unsatisfactory for the articles of the present invention. GB Pat. No. 2037735A proposes glasses comprising $P_2O_5$, cupric oxide and alkali metal oxide, the minimum quantity of $P_2O_5$ present is 45 mol% together with 5 to 55 mol% cupric oxide and alkali metal. In fact none of the specific examples contain alkali metal oxide, and the levels of cupric oxide in the three specific examples are in mol% 43.8 and 51.3. Such high levels of copper are not needed in the glass articles used in the treatment method of the present invention. The maximum preferred level of CuO is 36 mol% and it is more preferred that CuO be present in from 16 to 24 mol%. At these copper levels an article can readily be obtained for lodgement in the reticulo rumen with a lifetime of 6 to 12 months.

GB Pat. No. 2037735A relates primarily to glasses containing copper only and clearly teaches that the solubility of the glasses disclosed in that specification increases rapidly as the content of alkali metal oxide in the case of Na$_2$O exceeds 30% and in the case of K$_2$O exceeds 15%. Thus, with a minimum of 45 mol% $P_2O_5$ and a maximum alkali metal oxide content of 30 mol%, these glasses are in a different region to the glasses of the present invention. The only internal usage that is taught is as subcutaneous impants.

We prefer to use glasses in which the mol% ratio of $P_2O_5$:$R_2O$ is from 1.75:1 to 1:1.5, more desirably from 1.5:1 to 1:1.25. We particularly prefer glasses wherein the mol% ratio of $P_2O_5$:$R_2O$ is substantially 1:1, as this can be simply attained by using sodium metaphosphate or sodium hexametaphosphate as a batch ingredient when making up the glass batch for melting and forming into the glass article.

We have found that operating with levels of alkali metal oxide which are equivalent or substantially equivalent to the quantity of $P_2O_5$ used, we can form glasses whose rate of release in the rumen of an animal such as a sheep is such as to enable an article with the required life in the rumen to be formed. It is possible through the addition of other glass forming or modifying materials and one or more of the materials used to release trace elements to avoid the unsatisfactory solubility levels taught as occurring by GB Pat. No. 2037735A and U.S. Pat. No. 4,350,675 with levels of $Na_2O$ in excess of 30 mol%. It is also possible to incorporate more than one trace element in the glass article which, while clearly contemplated by the prior proposals, has never been actually demonstrated or exemplified as a practical possibility.

The influence of copper on the solubility in a reticulo rumen of sheep of a glass with a 1:1 $P_2O_5$ to $Na_2O$ ratio can be seen in Table I below. Each composition was formed into a glass melt by heating in a crucible at a temperature in the range 1000° to 1050° C., and then formed into an article having a length of 30 mm and a diameter of 14 mm. After annealing the articles were suspended via a fistula in the rumen of a sheep for test purposes to simulate insertion in the reticulo rumen and the release rate measured by determining the weight loss of the article in the rumen over a period which was dictated by the nature of the composition. Compositions with high release rates were removed after several hours so as to avoid excessive amounts of copper being assimilated by the sheep, compositions with lower release rates were removed after several days. This procedure was followed for all glass articles for which release rates in the rumen are given. At levels of CuO in the range 8 to 24 mol% it can be seen that these levels are too high and at the proportion of copper present would release too much copper and make it impracticable to produce an article of acceptable volume with a life of at least 3 months. As stated, we require a release rate of less than 25 mg/cm$^2$/day, having found that a glass with such a release rate can be made into an article which is of such a volume that it can easily be placed in the reticulo rumen of even a lamb.

Treatment with copper can be given to animals which are readily accessible by adding copper salts to their drinking water, or by giving injections. However, in the case of animals which are grazing over large areas, any individual treatment requires that they must be gathered together and the advantage of the present invention is that such treatments can be at relatively prolonged intervals. There is also no danger of exceeding the acceptable level of copper as can happen when an animal with a satisfactory copper level is injected, and poisoning the animal, as the copper is released in a controlled manner from the article placed in the rumen. The emphasis on copper is that the most widely occurring deficiency in ruminant animals worldwide requiring supplementing is copper. It is however unusual for only one deficiency to occur and to require treatment alone. The most usual deficiencies needing treatment are two or more of the following—copper, selenium, cobalt, zinc, iodine. The most widely needed combination which could not heretofore be treated by a single treatment is copper, selenium and cobalt.

In certain areas of the world copper is controlled by application of copper sulphate with fertiliser, e.g. Western Australia. In such an area only selenium and cobalt would be required for sheep, with the possible addition of zinc and/or iodine.

Thus, in one preferred form of the invention the article contains at least two deficiency-remedying elements, desirably selected from Cu, Se, Co, Zn and I. A particularly useful article contains Cu, Se and Co. The invention thus enables an animal to be treated for more than one deficiency and for periods desirably between 3 months and a year. This provides a treatment method which can be easily fitted into the husbandry methods employed in any particular circumstance.

Table I illustrates the release rates obtained with a simple 3 component mixture $P_2O_5/Na_2O/CuO$ with copper levels in the range 0 to 40, and indicates that a change in the level of CuO is not sufficient to give an acceptable release rate except at a very high level of CuO i.e. 40 mol%.

One way of producing glass articles with a lower release rate is to add materials which are known to increase the durability of phosphate glasses. As any material is added one must reduce the level of an existing component and also take care to ensure that the glass composition is one which forms a glass and as a glass can be formed into the necessary shaped article for lodgement in the reticulo rumen in a commercially viable forming process. Table II illustrates how the quantity of glass dissolved from an article containing 24% CuO can vary as the quantity of $P_2O_5$ and $Na_2O$ is reduced from a total of 76% to 56% and one or more of CaO and MgO added to control solubility and provide glass forming or modifying components. We prefer where possible to use CaO and MgO as the additional glass forming or modifying materials as these are easily incorporated into the glass, and also are components which if assimilated by the animal cannot accumulate or have a harmful effect. $Al_2O_3$ is another additional glass forming or modifying material which can conveniently be used. Desirably, the additional glass forming or modifying materials are present in at least 8 mol%, preferably up to 35 mol% but more desirably up to 24 mol%.

As can be seen from Table II it is a relatively simple matter to select an appropriate composition to give a release rate which will provide a glass article at a volume capable of fitting in an animal's reticulo rumen for any desired lifetime. Clearly one would not select highly soluble glasses Nos. 6 and 7, nor glasses Nos. 14, 15 or 16 which are liable to cause problems in forming the glass. It can be seen that once at least 8 mol% CaO and/or MgO are introduced into a glass at the higher end of the $P_2O_5/Na_2O$ range a glass with a release rate below 25 mg/cm$^2$/day is obtained. The values for release rate are primarily a guide and cannot be used to determined fine differences in release rate between one composition and another. It is not possible to determine the actual uptake of copper for every composition referred to as this involves performing a copper balance on the animal, and it is only feasible to do this with a limited number of animals as they have to be kept under laboratory conditions and fed a copper free diet. The results of field trials referred to hereafter and the overall work on in vivo release rates from glass articles lodged in the reticulo rumen indicate there are no problems in assimilation by the animal. It can also be seen from the results in Table II that with a steady value of CuO of 24 mol%, once the quantity of CaO and/or MgO is greater than 8 mol% there is little change in release rate in comparison with the major change produced by the initial addition of 8 mol% CaO and/or MgO, and that as the total quantity of $P_2O_5$ and $Na_2O$ falls to 56 glass manufacture problems then become apparent. The effect of reducing the copper content from 24 to 8 while maintaining a constant value in a 1:1 proportion of $Na_2O + P_2O_5$ is demonstrated in:

Table III for $Na_2O + P_2O_5 = 76$
Table IV for $Na_2O + P_2O_5 = 72$

Table V for $Na_2O+P_2O_5=68$
Table VI for $Na_2O+P_2O_5=64$
Table VII for $Na_2O+P_2O_5=60$
Table VIII for $Na_2O+P_2O_5=56$ These tables illustrate that, as in the case of the glasses of Table II, at the upper end of the $Na_2O+P_2O_5$ range (the glasses shown in Table III to VI) there is no problem in selecting glasses with a satisfactory release rate, and even at the lowest amount of CuO examined (8 mol%) there are no problems in glass forming. Tables VII and VIII confirm that it is difficult to form glasses as the CuO level falls and the level of CaO and MgO increases to above 24. Thus, certain compositions are indicated as "Devit", i.e. devitrified with crystallisation taking place on casting the melt, or "Suspect", i.e. with streaks of devitrification or phase separation within the composition. Fifty-six mol% of $Na_2O+P_2O_5$ is thought to be the lowest level at which a glass according to the invention can be cast, and by adjusting the levels of MgO and CaO from those shown in Table VIII some workable glasses could be made.

Tables III to VIII illustrate compositions where the level of CuO is below 16; however, our preference is to select glasses with a CuO content in the range 16 to 24 mol% so that the glass articles can be made with a lifetime believed to be desired in the market place i.e. 6 to 12 months and also at a size compatible with the oesophagus of the animal in the reticulo rumen of which it is to be lodged.

The addition of other trace elements may also influence the rate of release. The influence of CoO on the release rate is slight and does not make the manufacture of glasses at the lower end of the range any easier. The glasses exemplified in Table IX illustrate this in respect of both copper containing and copper free glasses.

The effect of the addition of selenium is not measurable as the quantity required (analysed as metal) is of the order of 0.3%, and this will have no identifiable effect in examining the release rate in vivo of an article which contains enough CoO and/or CuO for at least 6 months. Table X shows the range of results obtained when examining several samples made from compositions containing selenium compared with similar compositions without selenium. It can be seen that within the range of the experiment it is not possible to point to any change due to the presence of Se. Hence at the levels at which Se is added its presence is not of any consequence as regards glass shaping or overall release rate, although a lower melt temperature (800°-850° C.) is desirable to prevent evaporation of the selenium.

The guidance given in the Tables already referred to and in Tables XI to XVII to follow enables the man practised in the art to select a glass composition with a release rate below 25 mg/cm$^2$/day taking into account the requirements of the animals being treated. It is clearly impossible to illustrate all the possible combinations and permutations. It is believed that sufficient compositions have been melted and tested to illustrate the value of glass compositions comprising $P_2O_5$ and $Na_2O$ and containing at least 56 mol% and not more than 92 mol% (76 mol% if CuO or ZnO are present) of these materials taken together. It is clear from Tables II to X that a satisfactory release rate can be obtained from such glasses when the ratio of $P_2O_5:Na_2O$ is 1:1. If this ratio is changed by increasing the quantity of $Na_2O$ relative to the quantity of $P_2O_5$, the release rate will be increased and this can then be balanced by adding other components which have been shown to increase the durability in order to obtain a glass with a release rate below 25 mg/cm$^2$/day. This is clearly an alternative available to the man practised in the art to obtain glass articles having the characteristics required for treating ruminant animals for relatively lengthy periods. It is again impossible to melt and test in vivo, all the permutations and combinations that are introduced by the use of these materials. Table XI illustrates, from a comparison of glasses Nos. 131 and 132, the effect on release rate of increasing the quantity of $Na_2O$ relative to the amount of $P_2O_5$. It also shows that glasses with an excess of $Na_2O$ over $P_2O_5$ having an acceptable release rate can be made. However, there is no real advantage in using such glasses as compositions having a suitable release rate are likely to need an increased number of components in the batch used to form the glass.

An increase in the quantity of $P_2O_5$ so that it exceeds the quantity of $Na_2O$ present in the glass can also be made. This, while extending the glass forming area, shows that as the quantity of $P_2O_5$ relative to the quantity of $Na_2O$ is increased the release rate falls. There is again no real advantage to be gained in using compositions where there is an excess of $P_2O_5$ as this will mean adding another batch component, phosphoric acid, or using a phosphate source which does not also add alkali oxide to the glass composition. Examples with an excess of $P_2O_5$ over $Na_2O$ are included in Table XII.

Table XIII illustrates that the addition of $B_2O_3$, $Al_2O_3$, ZnO and $MnO_2$ can be used to reduce the release rate of a glass. $SiO_2$ was found to have no effect and $ZrO_2$ which is used in the manufacture of alkali resistant glasses resulted in devitrification at levels comparable to the levels of the other materials employed. Some areas of the world are in fact deficient in manganese and for such areas, the addition of manganese may be required and the examples show that such a material can be present in the glasses of the present invention.

Again, Tables XI and XIII include glasses which are unsatisfactory for use because their release rates are too high, or because they were devitrified or suspect. This means that the man practised in the art can select within the composition area, compositions which will give true glasses, i.e. glasses showing neither devitrification nor phase separation with a required release rate. The moves necessary either to reduce or increase the release rate of any chosen composition are therefore clearly identified. It is important to select for use compositions which given true glasses as it is essential in producing articles for treatment of animals to attain a strict control of composition and subsequent annealing of the articles. This is so that each article is of the desired composition and hence release rate, and is annealed so that there is no possibility of breaking up within the animal due to stresses induced by incorrect annealing.

The use of either $K_2O$ or $Li_2O$ in place of $Na_2O$ is of course feasible without any major change as is the use of mixtures of any of $K_2O$, $Na_2O$ and $Li_2O$. In general the use of $K_2O$ or $Li_2O$ will increase the batch cost without any commensurate advantage, and we prefer therefore to use $Na_2O$. Table XIV illustrates the use of $K_2O$ and $Li_2O$.

As further exemplification of the invention, glass compositions were prepared from the raw materials given in parts by weight in the first section of Table XV. The mixtures were melted at 1000° to 1100° in a clay crucible and were then successfully cast into glass articles having compositions in mol% shown in the second section of Table XV. Table XV shows further glass compositions over a wide range of relative proportions that can be successfully cast. Each composition will release copper as it dissolves, at a rate lower than 25 mg/cm$^2$/day.

Glass compositions were prepared from the raw materials given in parts by weight in the first section of Table XVI. The mixtures were melted at 1000° to 1100° C. in a clay crucible and were then successfully cast into glass articles having compositions in mol% shown in the second section of Table XVI. The examples in Table XVI show that articles can successfully be cast with raw materials that will incorporate into the composition a range of different trace elements. In each case the article will release the respective trace element or elements in a controlled fashion as the article dissolves.

In the examples shown in Table XVII the raw materials shown in parts by weight were melted together at 1000° to 1100° C. and then cast into glass articles having the compositions shown in mol%.

Tests showed the articles to have the release rates shown in Table XVII, thus being capable of releasing high quantities of magnesium into the reticulo rumen of a ruminant animal as the article dissolves. Such articles are thus suitable for the treatment of hypo-magnesaemia.

The examples that follow include field trials showing the performance of glass articles according to the invention.

EXAMPLE 1

The following raw materials were mixed in the percentages by weight shown: $K_2CO_3$ 9.16, MgO 5.30, CaO 7.37, $(NaPO_3)_n$ 68.60, CuO 9.57.

The mixture was melted at 1000° to 1100° C. in a clay crucible and was then cast into glass articles, giving a glass with a composition in mol% of: $P_2O_5$ 29.98, $Na_2O$ 29.96, MgO 11.72, Ca 11.71, CuO 10.72, $K_2O$ 5.91. Two different sizes of articles were produced, one having a diameter of 1.4 cm, a length of 4 cm and a weight of 11 g; and the other having a diameter of 1.6 cm; a length of 4.8 cm and a weight of 27 g. The articles contained 7.75% by weight of copper. The solubilities of the smaller articles were examined in the in vitro and in vivo rumen by suspending the articles in the rumen by means of a nylon thread. The daily weight loss was found to be 2.5 mg/cm$^2$ in the in vitro rumen and 3.0 mg/cm$^2$ in the in vivo rumen, the values given being the means of seven day measurement periods.

EXAMPLE 2

The following raw materials in the percentages shown by weight, were used to form a batch composition: $K_2CO_3$ 7.93, MgO 4.60, CaO 6.37, $(NaPO_3)_n$ 59.28, $CuSO_4$ 21.82.

The mixture was melted at 1000° to 1100° C. in a clay crucible.

After melting the composition was cast into small and large glass articles having the measurements given in Example 1, the glass having the following composition in mol%: $Na_2O$ 28.98, $P_2O_5$ 28.96, MgO 11.39, CaO 11.33, CuO 13.63, $K_2O$ 5.73. The articles contained copper at a level of 10% by weight.

The solubilities of the smaller articles were again examined in the in vitro and in vivo rumen, and with an article having an initial weight of 11.32 g the daily weight loss was found to be 3.3 mg/cm$^2$ in the in vivo rumen and 5.8 mg/cm$^2$ in the in vitro rumen.

Copper balance tests were carried out on sheep using articles of various sizes in accordance with the compositions of this Example. In a first test an article having a weight of 15.27 g (7.76%Cu), a diameter of 1.4 cm, a length of 3.8 cm and a calculated release rate of 1.7 to 2.9 mg/cm$^2$/day was inserted into the reticulo rumen of sheep. The sheep were fed on a hay or dried grass/barley diet and over a three month period a negative copper balance of $-4.5$ to $-6.5$ mg of copper per day and after seven months of $-2.7$ mg/day were noted, more copper thus being excreted than was being taken in even seven months after the administration of the article.

In a second test an article having a weight of 26.91, g, a diameter of 1.6 cm, a length of 4.8 cm and a calculated release rate of 2.2 mg/cm$^2$/day was inserted into the reticulo rumen of a sheep and a copper balance of $-6.1\pm0.7$ mg of copper per day was noted over a four month period. The results confirm that the articles were releasing copper into the intestinal tract of the animal.

Other satisfactory sizes of glass articles which are easily lodged in the reticulo rumen and retained therein are as follows:

Articles with a taper to fit a balling gun

Lamp
  Diameter taper from 15 to 13 mm
  Length 40 mm
Ewe
  Diameter taper from 19 to 17 mm
  Length 50 mm
Cow
  Diameter taper from 26 to 24 mm
  Length 80 mm Non-tapered Articles Lamb
  Diameter 14 mm
  Length 40 mm
Ewe
  Diameter 18 mm
  Length 50 mm
Cow
  Diameter 25 mm
  Length 80 mm During trials of the use of these articles it has become clear that the volume and density of the articles is such that there is no problem arising from the articles being regurgitated out of the reticulo rumen, and thus being prevented from releasing the elements they contain for the designated life of the article. The density of the glasses disclosed herein fall in the range 2.5 to 3.0. This is within the ranges quoted by previous workers e.g. in GB Pat. No. 1030101 and U.S. Pat. No. 3,056,724 as being sufficient to ensure satisfactory retention by the animal in the rumen.

As well as measuring the dissolution rate in a sheep's rumen of the glass articles, the effectiveness of the articles in raising the level of the trace elements released as the glass dissolves and the consequential effect on the animal's well being has been examined in field trials. It is not necessarily gross deficiencies that cause problems, borderline deficiencies reduce performance and are in some cases related to an inefficient conversion of feed. It is also difficult to carry out controlled experiments on grazing animals as other factors affecting their growth performance and health can intervene in a non-uniform manner and some animals may not respond to treatment. However, it is believed that the following examples illustrate dramatically the effectiveness of the article.

EXAMPLE 3

At first sight a simple method is to compare the growth performance of an untreated animal as a control with a treated animal. This is however difficult to do, as the growth rate of one animal in relation to another can be affected by other circumstances. It is thought that one way of reducing the margin of error is to treat one of a pair of each of a series of twin lambs, and then compare growth rates. In this Example a series of seven twins was used, and one of each pair was treated with a copper containing glass articles of composition the same as glass No. 194 (Table XV) i.e. mol% $P_2O_5$ 29.65, $Na_2O$ 29.64, MgO 28.38 and CuO 12.33. The gain in weight over a four week period for the treated animals averaged at 4.57 kilograms, and for the untreated animals only at 2.64 kilograms.

EXAMPLE 4

Forty (40) one year old sheep that had previously been grazing on a positive cobalt pasture were deliberately moved onto land known to be cobalt deficient. They were all ear tagged and blood sampled before the move on May 12, 1982. Thirty of the animals were given a cobalt containing glass pellet of the following composition in mol%: $P_2O_5$ 34.9, $Na_2O$ 34.9, MgO 21.1, CaO 7.6, and CoO 1.5, the pellet being designed to counteract any effect from the cobalt deficiency in the pasture. The sheep were taken from the pasture on June 14, 1982 and again blood sampled. The change in Vitamin $B_{12}$ measured in the blood over the trial period was as follows:

|  | Start 12.5.82 Mean Vit. $B_{12}$ (pg/ml) | Finish 14.6.82 Mean Vit. $B_{12}$ (pg/ml) |
| --- | --- | --- |
| Controls | 705 ± 65 | 316 ± 43 |
| Treated Sheep | 673 ± 50 | 818 ± 60 |

The test shows the clear divergence in Vitamin $B_{12}$. There is a deficiency of this vitamin if the level falls below 300 pg/ml, six of the controls exhibited this low level, the other four were somewhat above it.

The treated sheep had high vitamin levels, of the order of 750 to 900 pg/ml, showing that the cobalt required for vitamin $B_{12}$ synthesis was being released from the pellet. At the finish of the test the appearance of the controls was such that in order to avoid an adverse effect on their health, all the animals were moved back to a non-cobalt deficient pasture.

EXAMPLE 5

Prior to grazing on low copper pasture seventeen ewes were treated with a copper containing glass article of the composition of glass No. 194, i.e. having a composition in mol% of: $P_2O_5$ 29.65, $Na_2O$ 29.64, MgO 28.38, CuO 12.33. The levels of blood copper, caeruloplasmin and superoxide dismutase were measured in samples taken on 22.11.81 before administering the glass article to each animal and at regular intervals thereafter until 9.10.82. The articles had a release rate of the order of 2.5 mg/cm²/day and were clearly no longer having an effect by 9.10.82. Accordingly, a further article was then lodged in the rumen of 10 of the animals. These articles were of glass No. 128, having the composition in mol% of: $P_2O_5$ 33.5, $Na_2O$ 33.5, MgO 8, CaO 4, CuO 20, CoO 0.97, Se 0.3. The resulting change in levels shows that the downward trend in levels due to the previous article having reached the end of its life has been reversed. The release rate of this second article was of the order of 2.5 mg/cm²/day, and the results show that with levels of copper oxide in the glass of 20 mol% this is sufficient to provide the trace copper required by the animal. Both first and second articles used weighed 35 gms, were 50 mm long and tapered from 19 to 17 mm in diameter. The measurements resulting from an examination of the blood samples taken are given in Table XVIII. It will be noted that the second articles contained selenium. The factor used to determine whether a selenium deficiency exists is the glutathione peroxidase level. This was measured in samples taken on Oct. 9, 1982, before administering the second articles and on samples taken on Nov. 7, 1982. A ram used as a control showed a drop, and of the ten ewes all except two showed an increase in the glutathione peroxidase level, showing that the article containing copper cobalt and selenium was releasing the selenium in a form which the animals could assimilate.

EXAMPLE 6

Trials were conducted on 16 lambs at a farm where the animals could be transferred to a pasture deficient in copper, cobalt and selenium. Three lambs were used as controls. The levels of blood copper, caeruloplasmin, superoxide dismutase and Vitamin $B_{12}$ were measured in samples taken from all the lambs before administering articles to the 13 test lambs on June 29, 1982, the articles having the following composition in mol%: $P_2O_5$ 32.8, $Na_2O$ 32.8, MgO 6.8, CaO 11.3, CuO 14.8, CoO 1.6, Se 0.3. The release rate of the articles was of the order of 3 mg/cm²/day. Further samples were taken on Sept. 2 and Nov. 5, 1982, and the results are given in Table XIX along with the results on the samples taken prior to treatment. The results show that the levels in all cases of the controls are dropping, and where because of the high start level, this is also occurring in the treated animals, the untreated animals are dropping more rapidly. The vitamin $B_{12}$ levels are being held at a higher level in the treated animals than in the controls. It will be noted that the weight gain of the treated animals is higher than that of the controls. The results clearly show the trace elements present in the glass are being released in a form that they can be assimilated by the animals.

EXAMPLE 7

The results reported in the preceding trials are all on sheep, which have been used as ruminant animals which can be more easily controlled and treated. The trace element deficiencies of other ruminants are similar in character and the requirements of e.g. beef and dairy cattle are well known. To illustrate use of the articles in cattle, twenty calves grazing on copper deficient pastures were treated with glass articles of the following compositions in mol%: $P_2O_5$ 32.95, $Na_2O$ 32.95, MgO 15.16, CaO 4.67, CuO 14.27. Twenty untreated calves were used as controls. Table XX shows the results of blood sampling on the dates shown, and indicates that copper deficiency in the treated animals was being remedied.

The foregoing Examples illustrate the incorporation of a variety of trace elements into many different glass compositions, and the efficacy of such compositions in the treatment of trace element deficiencies in ruminant animals. It will be appreciated that many similar compositions can be produced which will dissolve to release balanced quantities of required trace elements into the intestinal tract of a ruminant animal, and the man skilled in the art will readily be enabled to formulate such compositions on the basis of the teaching herein contained.

TABLE I (Amounts given in mol %)

| Glass No. | P$_2$O$_5$ | Na$_2$O | CuO | Release Rate mg/cm$^2$/day |
|---|---|---|---|---|
| 1 | 50 | 50 | 0 | 4120 |
| 2 | 46 | 46 | 8 | 3550 |
| 3 | 42 | 42 | 16 | 1550 |
| 4 | 38 | 38 | 24 | 163 |
| 5 | 30 | 30 | 40 | 15.6 |

TABLE II (Amounts given in mol %)

| Glass No. | P$_2$O$_5$ | Na$_2$O | MgO | CaO | CuO | Release Rate mg/cm$^2$/day |
|---|---|---|---|---|---|---|
| 6 | 38 | 38 | 0 | 0 | 24 | 163 |
| 7 | 36 | 36 | 0 | 4 | 24 | 40.5 |
| 8 | 34 | 34 | 4 | 4 | 24 | 11 |
| 9 | 34 | 34 | 0 | 8 | 24 | 6.5 |
| 10 | 32 | 32 | 0 | 12 | 24 | 3.2 |
| 11 | 32 | 32 | 8 | 4 | 24 | 2.7 |
| 12 | 32 | 32 | 4 | 8 | 24 | 1.3 |
| 13 | 30 | 30 | 4 | 12 | 24 | 2.6 |
| 14 | 28 | 28 | 0 | 20 | 24 | Devit. |
| 15 | 28 | 28 | 8 | 12 | 24 | Devit. |
| 16 | 28 | 28 | 12 | 8 | 24 | Devit. |

TABLE III (Amounts given in mol %)

| Glass No. | P$_2$O$_5$ | Na$_2$O | MgO | CaO | CuO | Release Rate mg/cm$^2$/day |
|---|---|---|---|---|---|---|
| 17 | 38 | 38 | 0 | 0 | 24 | 163 |
| 18 | 38 | 38 | 0 | 4 | 20 | 14.9 |
| 19 | 38 | 38 | 4 | 0 | 20 | 24.4 |
| 20 | 38 | 38 | 0 | 8 | 16 | 13.1 |
| 21 | 38 | 38 | 0 | 16 | 8 | 6.3 |
| 22 | 38 | 38 | 4 | 12 | 8 | 2.9 |
| 23 | 38 | 38 | 8 | 8 | 8 | 6.5 |
| 24 | 38 | 38 | 12 | 4 | 8 | 6.5 |

TABLE IV (Amounts given in mol %)

| Glass No. | P$_2$O$_5$ | Na$_2$O | MgO | CaO | CuO | Release Rate mg/cm$^2$/day |
|---|---|---|---|---|---|---|
| 25 | 36 | 36 | 0 | 4 | 24 | 240 |
| 26 | 36 | 36 | 4 | 4 | 20 | 2.6 |
| 27 | 36 | 36 | 8 | 4 | 16 | 5.6 |
| 28 | 36 | 36 | 0 | 12 | 16 | 5.5 |
| 29 | 36 | 36 | 4 | 8 | 16 | 2.7 |
| 30 | 36 | 36 | 8 | 8 | 12 | 4.8 |
| 31 | 36 | 36 | 0 | 16 | 12 | 6.0 |
| 32 | 36 | 36 | 16 | 0 | 12 | 6.0 |
| 33 | 36 | 36 | 0 | 20 | 8 | 5.7 |
| 34 | 36 | 36 | 4 | 16 | 8 | 4.3 |
| 35 | 36 | 36 | 8 | 12 | 8 | 6.0 |

TABLE V (Amounts given in mol %)

| Glass No. | P$_2$O$_5$ | Na$_2$O | MgO | CaO | CuO | Release Rate mg/cm$^2$/day |
|---|---|---|---|---|---|---|
| 36 | 34 | 34 | 0 | 0 | 32 | 22 |
| 37 | 34 | 34 | 4 | 4 | 24 | 11 |
| 38 | 34 | 34 | 0 | 8 | 24 | 6.5 |
| 39 | 34 | 34 | 0 | 12 | 20 | 4.5 |
| 40 | 34 | 34 | 8 | 4 | 20 | 2.8 |
| 41 | 34 | 34 | 12 | 0 | 20 | 4.1 |
| 42 | 34 | 34 | 4 | 8 | 20 | 3.2 |
| 43 | 34 | 34 | 0 | 16 | 16 | 3.9 |
| 44 | 34 | 34 | 12 | 4 | 16 | 2.5 |
| 45 | 34 | 34 | 8 | 8 | 16 | 2.6 |
| 46 | 34 | 34 | 0 | 24 | 8 | 6.2 |
| 47 | 34 | 34 | 4 | 20 | 8 | 2.0 |
| 48 | 34 | 34 | 8 | 16 | 8 | 5.8 |
| 49 | 34 | 34 | 12 | 12 | 8 | 2.2 |

TABLE VI (Amounts given in mol %)

| Glass No. | P$_2$O$_5$ | Na$_2$O | MgO | CaO | CuO | Release Rate mg/cm$^2$/day |
|---|---|---|---|---|---|---|
| 50 | 32 | 32 | 0 | 4 | 32 | 6.2 |
| 51 | 32 | 32 | 0 | 12 | 24 | 3.2 |
| 52 | 32 | 32 | 4 | 8 | 24 | 1.3 |
| 53 | 32 | 32 | 8 | 4 | 24 | 2.7 |
| 54 | 32 | 32 | 8 | 4 | 24 | 2.8 |
| 55 | 32 | 32 | 8 | 8 | 20 | 2.3 |
| 56 | 32 | 32 | 16 | 0 | 20 | 3.2 |
| 57 | 32 | 32 | 4 | 16 | 16 | 4.2 |
| 58 | 32 | 32 | 8 | 12 | 16 | 4.5 |
| 59 | 32 | 32 | 12 | 8 | 16 | 2.2 |
| 60 | 32 | 32 | 16 | 8 | 12 | 3.3 |
| 61 | 32 | 32 | 8 | 16 | 12 | 4.5 |
| 62 | 32 | 32 | 12 | 16 | 8 | 2.6 |
| 63 | 32 | 32 | 8 | 20 | 8 | 2.7 |
| 64 | 32 | 32 | 28 | 0 | 8 | Suspect |
| 65 | 32 | 32 | 0 | 24 | 12 | Devit. |

TABLE VII (Amounts given in mol %)

| Glass No. | P$_2$O$_5$ | Na$_2$O | MgO | CaO | CuO | Release Rate mg/cm$^2$/day |
|---|---|---|---|---|---|---|
| 66 | 30 | 30 | 0 | 0 | 40 | 22.5 |
| 67 | 30 | 30 | 0 | 8 | 32 | 5.6 |
| 68 | 30 | 30 | 0 | 16 | 24 | Suspect |
| 69 | 30 | 30 | 4 | 12 | 24 | 2.6 |
| 70 | 30 | 30 | 12 | 4 | 24 | 1.2 |
| 71 | 30 | 30 | 0 | 20 | 20 | Devit. |
| 72 | 30 | 30 | 4 | 16 | 20 | Devit. |
| 73 | 30 | 30 | 16 | 4 | 20 | 2.5 |
| 74 | 30 | 30 | 12 | 8 | 20 | 3.3 |
| 75 | 30 | 30 | 4 | 24 | 16 | Devit. |
| 76 | 30 | 30 | 4 | 20 | 16 | Devit. |
| 77 | 30 | 30 | 8 | 16 | 16 | 6.7 |
| 78 | 30 | 30 | 12 | 12 | 16 | 7.3 |
| 79 | 30 | 30 | 8 | 24 | 8 | Devit. |
| 80 | 30 | 30 | 12 | 20 | 8 | Devit. |
| 81 | 30 | 30 | 32 | 0 | 8 | Suspect |

TABLE VIII (Amounts given in mol %)

| Glass No. | P$_2$O$_5$ | Na$_2$O | MgO | CaO | CuO | Release Rate mg/cm$^2$/day |
|---|---|---|---|---|---|---|
| 82 | 28 | 28 | 0 | 0 | 44 | Suspect |
| 83 | 28 | 28 | 0 | 4 | 40 | Suspect |
| 84 | 28 | 28 | 0 | 12 | 32 | Devit. |
| 85 | 28 | 28 | 8 | 4 | 32 | Suspect |
| 86 | 28 | 28 | 0 | 20 | 24 | Devit. |
| 87 | 28 | 28 | 8 | 12 | 24 | Devit. |
| 88 | 28 | 28 | 12 | 8 | 24 | Suspect |
| 89 | 28 | 28 | 4 | 16 | 24 | Devit. |
| 90 | 28 | 28 | 4 | 20 | 20 | Devit. |
| 91 | 28 | 28 | 0 | 28 | 16 | Devit. |
| 92 | 28 | 28 | 12 | 16 | 16 | Devit. |
| 93 | 28 | 28 | 16 | 16 | 12 | Devit. |

TABLE VIII-continued (Amounts given in mol %)

| Glass No. | P$_2$O$_5$ | Na$_2$O | MgO | CaO | CuO | Release Rate mg/cm$^2$/day |
|---|---|---|---|---|---|---|
| 94 | 28 | 28 | 4 | 32 | 8 | Devit. |
| 95 | 28 | 28 | 8 | 28 | 8 | Devit. |
| 96 | 28 | 28 | 12 | 24 | 8 | Devit. |

TABLE IX (Amounts given in mol %)

| Glass No. | P$_2$O$_5$ | Na$_2$O | MgO | CaO | CuO | CoO | Release Rate mg/cm$^2$/day |
|---|---|---|---|---|---|---|---|
| 97 | 42 | 42 | 8 | 8 | 0 | 0 | 288 |
| 98 | 42 | 42 | 6 | 8 | 0 | 2 | 6.6 |
| 99 | 42 | 42 | 4 | 8 | 0 | 4 | 10.6 |
| 100 | 38 | 38 | 8 | 16 | 0 | 0 | 128 |
| 101 | 38 | 38 | 6 | 16 | 0 | 2 | 4.5 |
| 102 | 38 | 38 | 4 | 16 | 0 | 4 | 5.5 |
| 103 | 42 | 42 | 8 | 8 | 0 | 0 | 288 |
| 104 | 42 | 42 | 8 | 6 | 0 | 2 | 8.8 |
| 105 | 42 | 42 | 8 | 4 | 0 | 4 | 8.7 |
| 106 | 38 | 38 | 8 | 16 | 0 | 0 | 128 |
| 107 | 38 | 38 | 8 | 14 | 0 | 2 | 3.8 |
| 108 | 38 | 38 | 8 | 12 | 0 | 4 | 4.8 |
| 109 | 34 | 34 | 4 | 4 | 24 | 0 | 11 |
| 110 | 34 | 34 | 4 | 4 | 22 | 2 | 5.0 |
| 111 | 34 | 34 | 4 | 4 | 20 | 4 | 2.4 |
| 112 | 38 | 38 | 0 | 8 | 16 | 0 | 13 |
| 113 | 38 | 38 | 0 | 8 | 14 | 2 | 5.7 |
| 114 | 38 | 38 | 0 | 8 | 12 | 4 | 4.6 |
| 115 | 40 | 40 | 0 | 12 | 8 | 0 | 13 |
| 116 | 40 | 40 | 0 | 12 | 6 | 2 | 9.6 |
| 117 | 40 | 40 | 0 | 12 | 4 | 4 | 8.4 |
| 118 | 46 | 46 | 8 | 0 | 0 | 0 | 970 |
| 119 | 45 | 45 | 8 | 0 | 0 | 2 | 51.3 |
| 120 | 44 | 44 | 8 | 0 | 0 | 4 | 9.7 |
| 121 | 42 | 42 | 8 | 8 | 0 | 0 | 288 |
| 122 | 41 | 41 | 8 | 8 | 0 | 2 | 4.0 |
| 123 | 40 | 40 | 8 | 8 | 0 | 4 | 3.1 |
| 124 | 38 | 38 | 8 | 16 | 0 | 0 | 128 |
| 125 | 37 | 37 | 8 | 16 | 0 | 2 | 15.5 |
| 126 | 36 | 36 | 8 | 16 | 0 | 4 | 1.5 |

TABLE X (Amounts given in mol %)

| Glass No. | P$_2$O$_5$ | Na$_2$O | MgO | CaO | CuO | ZnO | CoO | Se | Release Rate* mg/cm$^2$/day |
|---|---|---|---|---|---|---|---|---|---|
| 127 | 33.5 | 33.5 | 8 | 4 | 20 | 0 | 1 | 0 | 2.53 |
| 128 | 33.5 | 33.5 | 8 | 4 | 20 | 0 | 0.97 | 0.3 | 2.53 |
| 129 | 35.5 | 35.5 | 4 | 4 | 0 | 20 | 1 | 0 | 2.60 |
| 130 | 35.5 | 35.5 | 4 | 4 | 0 | 20 | 0.97 | 0.3 | 2.69 |

*In each case the release rate given is the average of three different samples each having the same mol % composition.

TABLE XI (Amounts given in mol %)

| Glass No. | P$_2$O$_5$ | Na$_2$O | MgO | CaO | Al$_2$O$_3$ | CuO | Release Rate mg/cm$^2$/day |
|---|---|---|---|---|---|---|---|
| 131 | 36 | 36 | 4 | 8 | 0 | 16 | 2.7 |
| 132 | 36 | 44 | 4 | 0 | 0 | 16 | 178 |
| 133 | 36 | 44 | 0 | 4 | 0 | 16 | 487 |
| 134 | 35 | 43 | 0 | 4 | 2 | 16 | 32 |
| 135 | 34 | 42 | 0 | 4 | 4 | 16 | 16 |
| 136 | 33 | 41 | 0 | 4 | 6 | 16 | 0.8 |
| 137 | 32 | 40 | 0 | 4 | 8 | 16 | 0.2 |

TABLE XII (Amounts given in mol %)

| Glass No. | P$_2$O$_5$ | Na$_2$O | MgO | CaO | CuO | Release Rate mg/cm$^2$/day |
|---|---|---|---|---|---|---|
| 138 | 44 | 36 | 0 | 12 | 8 | 22 |
| 139 | 46 | 30 | 0 | 0 | 24 | 12 |
| 140 | 44 | 32 | 0 | 0 | 24 | 6.1 |
| 141 | 42 | 34 | 0 | 8 | 16 | 5.7 |
| 142 | 42 | 34 | 0 | 0 | 24 | 12.1 |
| 143 | 42 | 34 | 0 | 16 | 8 | 3.5 |
| 144 | 40 | 32 | 0 | 20 | 8 | 4.3 |
| 145 | 40 | 32 | 0 | 4 | 24 | 12.1 |
| 146 | 38 | 30 | 0 | 8 | 24 | 2.4 |
| 147 | 38 | 30 | 0 | 24 | 8 | 1.0 |
| 148 | 38 | 30 | 0 | 16 | 16 | 1.4 |
| 149 | 36 | 28 | 0 | 28 | 8 | 2.1 |
| 150 | 36 | 24 | 0 | 16 | 20 | 3.0 |
| 151 | 36 | 28 | 0 | 8 | 28 | 2.1 |
| 152 | 36 | 28 | 0 | 0 | 36 | 1.8 |
| 153 | 32 | 24 | 8 | 0 | 36 | 1.0 |

TABLE XIII (Amounts given in mol %)

| Glass No. | Other Component | | P$_2$O$_5$ | Na$_2$O | MgO | CaO | CuO | Release Rate mg/cm$^2$/day |
|---|---|---|---|---|---|---|---|---|
| 154 | — | | 40.0 | 40.0 | 0 | 0 | 20 | 400 |
| 155 | B$_2$O$_3$ | 5 | 37.5 | 37.5 | 0 | 0 | 20 | 35 |
| 156 | B$_2$O$_3$ | 10 | 35 | 35 | 0 | 0 | 20 | 1.0 |
| 157 | Al$_2$O$_3$ | 5 | 37.5 | 37.5 | 0 | 0 | 20 | 1.0 |
| 158 | Al$_2$O$_3$ | 10 | 35 | 35 | 0 | 0 | 20 | 0.6 |
| 159 | SiO$_2$ | 10 | 35 | 35 | 0 | 0 | 20 | 213 |
| 160 | ZnO$_2$ | 5 | 37.5 | 37.5 | 0 | 0 | 20 | Devit. |
| 161 | ZnO$_2$ | 10 | 35 | 35 | 0 | 0 | 20 | Devit. |
| 162 | ZnO | 5 | 37.5 | 37.5 | 0 | 0 | 20 | 40 |
| 163 | ZnO | 10 | 35 | 35 | 0 | 0 | 20 | 2.8 |
| 164 | MnO$_2$ | 5 | 37.5 | 37.5 | 0 | 0 | 20 | 60 |
| 165 | MnO$_2$ | 10 | 35 | 35 | 0 | 0 | 20 | 20 |
| 166 | — | | 34 | 34 | 8 | 4 | 20 | 5.7 |
| 167 | ZnO | 20 | 34 | 34 | 8 | 4 | 0 | 1.6 |
| 168 | Al$_2$O$_3$ | 20 | 34 | 34 | 8 | 4 | 0 | 1.5 |
| 169 | Al$_2$O$_3$ ZnO | 10 10 | 34 | 34 | 8 | 4 | 0 | 0.13 |
| 170 | ZnO | 20 | 32 | 32 | 8 | 8 | 0 | 0.4 |
| 171 | ZnO | 20 | 30 | 30 | 12 | 8 | 0 | Devit. |
| 172 | ZnO | 20 | 30 | 30 | 8 | 12 | 0 | Devit. |
| 173 | ZnO | 20 | 36 | 36 | 4 | 4 | 0 | 2.2 |
| 174 | ZnO | 20 | 36 | 36 | 0 | 8 | 0 | 4.2 |
| 175 | ZnO | 20 | 36 | 36 | 0 | 8 | 0 | 2.2 |
| 176 | ZnO | 20 | 38 | 38 | 4 | 0 | 0 | 17 |
| 177 | ZnO | 20 | 38 | 38 | 0 | 4 | 0 | 11.7 |

TABLE XIV (Amounts given in mol %)

| Glass No. | P₂O₅ | Na₂O | K₂O | Li₂O | MgO | CaO | CuO | CoO | Release Rate mg/cm²/day |
|---|---|---|---|---|---|---|---|---|---|
| 178 | 33.5 | 33.5 | 0 | 0 | 8 | 4 | 20 | 1 | 2.4 |
| 179 | 33.5 | 0 | 33.5 | 0 | 8 | 4 | 20 | 1 | 79 |
| 180 | 33.5 | 0 | 0 | 33.5 | 8 | 4 | 20 | 1 | 0.3 |
| 181 | 34 | 34 | 0 | 0 | 4 | 8 | 20 | 0 | 2.1 |
| 182 | 33 | 33 | 2 | 0 | 4 | 8 | 20 | 0 | 4.2 |
| 183 | 32 | 32 | 4 | 0 | 4 | 8 | 20 | 0 | 5.3 |
| 184 | 33 | 33 | 0 | 2 | 4 | 8 | 20 | 0 | 4.2 |
| 185 | 32 | 32 | 0 | 4 | 4 | 8 | 20 | 0 | 5.2 |
| 186 | 33 | 35 | 0 | 0 | 4 | 8 | 20 | 0 | 3.7 |
| 187 | 33 | 37 | 0 | 0 | 4 | 8 | 20 | 0 | 8.3 |

TABLE XV

| | Weight % | | | | | | | Mol % | | | | | |
|---|---|---|---|---|---|---|---|---|---|---|---|---|---|
| Glass No. | (NaPO₄)₆ | (NaPO₃)ₙ | MgO | CaO | K₂CO₃ | CuO | CuSO₄ | Na₂O | P₂O₅ | MgO | CaO | K₂O | CuO |
| 188 | 69.2 | 0 | 4.73 | 6.56 | 8.16 | 11.35 | 0 | 30.44 | 30.42 | 10.54 | 10.51 | 5.30 | 12.80 |
| 189 | 0 | 66.33 | 5.14 | 7.14 | 8.86 | 12.53 | 0 | 28.87 | 28.84 | 11.32 | 11.31 | 5.70 | 13.97 |
| 190 | 0 | 69.40 | 5.50 | 7.60 | 4.70 | 12.80 | 0 | 29.66 | 29.65 | 11.89 | 11.83 | 2.96 | 14.02 |
| 191 | 77.8 | 0 | 4.30 | 6.20 | 0 | 11.70 | 0 | 33.84 | 33.83 | 9.47 | 9.81 | 0 | 13.05 |
| 192 | 73.13 | 0 | 3.00 | 12.42 | 0 | 11.45 | 0 | 30.99 | 30.98 | 6.43 | 19.15 | 0 | 12.44 |
| 193 | 76.40 | 0 | 0 | 12.00 | 0 | 11.60 | 0 | 33.78 | 33.76 | 0 | 19.31 | 0 | 13.15 |
| 194 | 74.00 | 0 | 14.00 | 0 | 0 | 12.00 | 0 | 29.65 | 29.64 | 28.38 | 0 | 0 | 12.33 |
| 195 | 0 | 74.41 | 9.31 | 0 | 8.05 | 8.23 | 0 | 32.51 | 32.50 | 20.58 | 0 | 5.19 | 9.23 |
| 196 | 71.80 | 0 | 2.05 | 8.53 | 0 | 17.62 | 0 | 31.20 | 31.18 | 4.51 | 13.49 | 0 | 19.63 |
| 197 | 72.51 | 0 | 4.13 | 5.75 | 0 | 17.61 | 0 | 31.27 | 31.24 | 9.01 | 9.02 | 0 | 19.47 |
| 198 | 78.18 | 0 | 5.56 | 4.64 | 0 | 11.62 | 0 | 33.83 | 33.81 | 12.17 | 7.30 | 0 | 12.89 |
| 199 | 0 | 56.06 | 4.42 | 6.67 | 7.50 | 0 | 25.35 | 27.73 | 27.71 | 11.07 | 12.01 | 5.47 | 16.02 |
| 200 | 0 | 62.42 | 4.93 | 6.71 | 8.35 | 0 | 17.59 | 29.87 | 29.85 | 11.94 | 11.68 | 5.90 | 10.76 |

TABLE XVI

| Glass No.:- | 201 | 202 | 203 | 204 | 205 | 206 | 207 | 208 | 209 |
|---|---|---|---|---|---|---|---|---|---|
| Weight % | | | | | | | | | |
| (NaPO₄)₆ | 72.79 | 74.55 | 83.00 | 84.40 | 73.70 | 77.30 | 76.00 | 68.80 | 68.60 |
| MgO | 5.31 | 5.00 | 16.40 | 14.40 | 12.70 | 4.20 | 4.00 | 4.70 | 4.60 |
| CaO | 7.39 | 7.08 | 0 | 0 | 0 | 6.10 | 6.00 | 6.50 | 6.50 |
| K₂CO₃ | 9.19 | 8.82 | 0 | 0 | 0 | 0 | 0 | 8.10 | 8.00 |
| CoSO₄ | 9.32 | 0 | 0 | 0 | 0 | 0 | 0 | 0.60 | 0.60 |
| Se | 0 | 4.55 | 0 | 0 | 0 | 0 | 0 | 0 | 0.40 |
| KI | 0 | 0 | 0.60 | 1.20 | 13.60 | 0 | 0 | 0 | 0 |
| CuI | 0 | 0 | 0 | 0 | 0 | 0.80 | 2.60 | 0 | 0 |
| CuO | 0 | 0 | 0 | 0 | 0 | 11.60 | 11.40 | 11.30 | 11.30 |
| Mol % | | | | | | | | | |
| Na₂O | 32.33 | 33.17 | 33.24 | 34.72 | 32.28 | 33.75 | 33.42 | 30.35 | 30.26 |
| P₂O₅ | 32.31 | 33.14 | 33.23 | 34.70 | 32.26 | 33.74 | 33.39 | 30.34 | 30.25 |
| MgO | 11.94 | 11.24 | 33.24 | 29.97 | 28.15 | 9.28 | 8.90 | 10.49 | 10.28 |
| CaO | 11.95 | 11.45 | 0 | 0 | 0 | 9.69 | 9.60 | 10.43 | 10.43 |
| K₂O | 6.02 | 5.79 | 0.15 | 0.30 | 3.66 | 0 | 0 | 5.27 | 5.21 |
| CuO | 0 | 0 | 0 | 0 | 0 | 13.36 | 14.08 | 12.78 | 12.78 |
| CoO | 5.46 | 0 | 0 | 0 | 0 | 0 | 0 | 0.35 | 0.35 |
| Se | 0 | 5.21 | 0 | 0 | 0 | 0 | 0 | 0 | 0.45 |
| I₂ | 0 | 0 | 0.15 | 0.30 | 3.66 | 0.19 | 0.61 | 0 | 0 |

TABLE XVII

| Glass No. | 210 | 211 | 212 |
|---|---|---|---|
| Materials by weight | | | |
| (NaPO₄)₆ | 85.40 | 83.50 | 78.00 |
| MgO | 14.60 | 16.50 | 22.00 |
| Composition mol % | | | |
| Na₂O | 34.91 | 33.35 | 29.18 |
| P₂O₅ | 34.90 | 33.32 | 29.17 |
| MgO | 30.20 | 33.33 | 41.65 |
| Release Rate (mg/cm²/day) | 8.0 | 10.0 | 20.0 |

TABLE XVIII

| Date | Week | BLOOD COPPER Cu μg/100 ml plasm | HAEMOGLOBIN Hb g/100 ml blood | CAERULOPLASMIN C P mg/100 ml plasma | SUPEROXIDE DISMUTASE S O D units/grams of haemoglobin |
|---|---|---|---|---|---|
| 22.11.81 | 0 | 80.0 ± 4.5 | 14.98 ± 0.31 | 26.24 ± 3.54 | 1204 ± 70 |
| 20.12.81 | 4 | 79.7 ± 5.2 | 16.21 ± 0.38 | 50.06 ± 3.90 | 1249 ± 55 |
| 7.1.82 | 7 | 93.8 ± 4.8 | 16.54 ± 0.34 | 37.30 ± 2.59 | 1300 ± 90 |
| 7.2.82 | 11 | 86.2 ± 4.5 | 15.20 ± 0.27 | 26.18 ± 3.63 | 1523 ± 147 |
| 20.3.82 | 17 | 76.2 ± 4.6 | 12.86 ± 0.30 | 32.88 ± 4.04 | 1529 ± 165 |
| 24.4.82 | 22 | 76.5 ± 4.9 | 14.00 ± 0.27 | 27.71 ± 2.95 | 1731 ± 185 |
| 31.5.82 | 27 | 79.1 ± 6.2 | 12.71 ± 0.40 | 17.60 ± 2.29 | 1768 ± 196 |
| 10.7.82 | 33 | 88.8 ± 7.3 | 13.48 ± 0.29 | 18.77 ± 2.85 | 1483 ± 185 |
| 6.8.82 | 37 | 77.6 ± 6.7 | 12.36 ± 0.36 | 21.18 ± 2.76 | 1469 ± 162 |
| 31.8.82 | 41 | 61.8 ± 8.1 | 12.57 ± 0.34 | 18.82 ± 2.97 | 1394 ± 169 |

TABLE XVIII-continued

| Date | Week | BLOOD COPPER Cu μg/100 ml plasm | HAEMOGLOBIN Hb g/100 ml blood | CAERULOPLASMIN C P mg/100 ml plasma | SUPEROXIDE DISMUTASE S O D units/grams of haemoglobin |
|---|---|---|---|---|---|
| 9.10.82* | 47 | 50.0 ± 5.45 | 11.97 ± 0.21 | 14.72 ± 2.88 | 1189 ± 147 |
| 7.11.82 | 51 | 76.4 ± 3.10 | 12.16 ± 0.23 | 28.9 ± 2.33 | 1400 ± 127 |
| 5.12.82 | 55 | 77.0 ± 3.3 | 13.40 ± 0.36 | 31.9 ± 1.48 | 1446 ± 118 |

*Second article administered on 9.10.82 after blood sampling.

TABLE XIX

| Lambs Date Sampled | Plasma Cu μg/100 ml | | Caeruloplasmin mg/100 ml | | Superoxide dismutase units/g Haemoglobin | |
|---|---|---|---|---|---|---|
| | + Bullet | Control | + Bullet | Control | + Bullet | Control |
| 29.6.82 | 107 ± 8 | 100 ± 6 | 33 ± 3 | 34 ± 2 | 2120 ± 75 | 1900 ± 168 |
| 2.9.82 | 98 ± 2 | 70 ± 6 | 32 ± 3 | 22 ± 5 | 2042 ± 76 | 1500 ± 208 |
| 5.11.82 | 95 ± 4 | 50 ± 6 | 31 ± 2 | 13 ± 4 | 2034 ± 55 | 1273 ± 151 |

| | Haemoglobin % | | Liveweight kg | | Vit $B_{12}$ pg/ml | |
|---|---|---|---|---|---|---|
| | +Bullet | Control | + Bullet | Control | + Bullet | Control |
| 29.6.82 | 16.2 ± 0.7 | 16.4 ± 1 | 19.7 ± 1.4 | 20.2 ± 1.9 | 2076 ± 312 | 1253 ± 48 |
| 2.9.82 | 16 ± 0.6 | 14 ± 0.8 | 29.2 ± 1.5 | 26.8 ± 2.3 | 1556 ± 218 | 1069 ± 216 |
| 5.11.82 | 15.9 ± 0.4 | 13.6 ± 0.4 | — | — | — | — |

TABLE XX

| | Date | Treated | Controls |
|---|---|---|---|
| Plasma Cu μg/100 ml | 16.6.82 | 81 ± 7 | 71 ± 7 |
| | 16.7.82 | 87 ± 6 | 71 ± 5 |
| | 26.8.82 | 80 ± 4 | 66 ± 7 |
| | 22.9.82 | 116 ± 5 | 82 ± 6 |
| Caeruloplasmin mg/100 ml plasma | 16.6.82 | 24 ± 3 | 20 ± 3 |
| | 16.7.82 | 30 ± 2 | 14 ± 3 |
| | 26.8.82 | 31 ± 2 | 11 ± 2 |
| | 22.9.82 | 34 ± 2 | 14 ± 2 |
| Superoxide Dismutase units/g HB | 16.6.82 | 2602 ± 92 | 2553 ± 142 |
| | 16.7.82 | 2940 ± 137 | 2565 ± 130 |
| | 26.8.82 | 2915 ± 76 | 1923 ± 72 |
| | 22.9.82 | 3055 ± 50 | 1983 ± 55 |
| Haemoglobin (Hb) % | 16.6.82 | 14.6 ± 0.3 | 14.7 ± 0.5 |
| | 16.7.82 | 15.7 ± 0.2 | 14.1 ± 0.8 |
| | 26.8.82 | 15.6 ± 0.2 | 13.9 ± 0.6 |
| | 22.9.82 | 15.7 ± 0.1 | 14.6 ± 0.2 |
| Liveweight (kg) | 16.6.82 | 89.5 ± 5.7 | 88.9 ± 6.2 |
| | 16.7.82 | 116.2 ± 5.8 | 117.9 ± 6.6 |
| | 26.8.82 | 165.6 ± 6.9 | 162.8 ± 7.6 |
| | 22.9.82 | 189.2 ± 6.4 | 193.4 ± 8.0 |

We claim:

1. A water soluble glass article in a form suitable for administration to a ruminant animal, the article containing:

(a) $P_2O_5$ (b) $R_2O$ where R is chosen from Na, K and Li (c) at least one other glass modifying or forming material (d) at least one deficiency-rectifying element combined in the glass, said element being selected from Cu, Se, Co, Zn, I, Mn and Mg in which:

when CuO is present in the glass the content of each of $P_2O_5$ and $R_2O$ does not exceed 45 mol%;

when at least one of CuO and ZnO is present in the glass the sum of the quantities of $P_2O_5$ and $R_2O$ is in the range of 56–76 mol%;

when CuO and ZnO are absent and at least one of MgO, CoO, SeO and I is present in the glass the sum of the quantities of $P_2O_5$ and $R_2O$ is in the range of 56–92 mol%;

and the composition being such that when the glass article is present in the reticulo rumen of the animal the article has a release rate of not more than 25 mg per square centimeter of article surface area per day.

2. An article according to claim 1 in which component (c) is present in at least 8 mol%.

3. An article according to claim 1 in which the mol% ratio of $P_2O_5:R_2O$ is from 1.75:1 to 1:1.5.

4. An article according to claim 1 in which the mol% ratio of $P_2O_5:R_2O$ is from 1.5:1 to 1:1.25.

5. An article according to claim 1 in which the mol% ratio of $P_2O_5:R_2O$ is substantially 1:1.

6. An article according to claim 1 in which at least one of sodium metaphosphate $(NaPO)_{3})_n$ and sodium hexametophosphate $(NaPO_4)_6$ has been used as the principal batch ingredient when making up the glass batch for melting and forming into the article.

7. An article according to claim 1 in which component (c) is chosen from CaO, MgO and $Al_2O_3$.

8. An article according to claim 7 in which component (c) is present in from 8 to 35 mol%.

9. An article according to claim 7 in which component (c) is present in from 8 to 24 mol%.

10. An article according to claim 1 in which CuO is present in not more than 36 mol%.

11. An article according to claim 1 in which CuO is present in from 16 to 24 mol%.

12. An article according to claim 1 in which component (d) comprises at least two of said deficiency-remedying elements.

13. An article according to claim 12 in which component (d) comprises at least two elements selected from Cu, Se, Co, Zn and I.

14. An article according to claim 12, containing Cu, Se and Co as deficiency-remedying elements.

15. An article according to claim 1 in which component (c) is one only other glass forming or modifying material and component (d) is combined in said other glass forming or modifying material.

16. An article according to claim 15 in which component (c) is CuO and the deficiency-rectifying element is copper.

17. An article according to claim 16 in which component (c) is MgO and the deficiency-rectifying element is magnesium.

18. A method of forming a water-soluble glass article according to claim 1 comprising mixing as batch ingredients
  (i) a compound selected from sodium metaphosphate and sodium hexametaphosphate
  (ii) at least one other glass forming or modifying material
  (ii) at least one material incorporating a deficiency-rectifying element selected from Cu, Se, Co, Zn, I, Mn and Mg,
heating the materials to a glass forming temperature and forming the glass composition into an article of the required physical form.

19. A method of remedying an element deficiency in a ruminant animal comprising lodging in the reticulo rumen of the animal an article according to claim 1.

20. A water soluble glass article containing:
  (i) from 28 to 38 mol% of $P_2O_5$
  (ii) an equal amount of $Na_2O$
  (iii) from 8 to 24 mol% of glass forming or modifying material selected from CaO, MgO, $Al_2O_3$ and combinations thereof
  (iv) from 16 to 24 mol% of CuO.

21. An article according to claim 20 and containing at least one further deficiency-rectifying element combined in the glass, said element being selected from Se, Co, Zn, I and Mn.

22. An article according to claim 20 and also containing up to 4 mol% of CoO.

23. An article according to claim 22 and also containing selenium.

24. A method of forming a water-soluble glass article according to claim 20 comprising mixing as batch ingredients
  (i) a compound selected from sodium metaphosphate and sodium hexametaphosphate
  (ii) at least one compound selected from CaO, MgO and $Al_2O_3$
  (iii) a compound selected from CuO and $CuSO_4$ heating the materials to a glass forming temperature and forming the glass composition into an article of the required physical form.

25. A method according to claim 24 in which the batch ingredients also include material which will incorporate into the glass a deficiency-remedying element selected from Se, Co, Zn, I, Mn and Mg.

26. A method of remedying an element deficiency in a ruminant animal comprising lodging in the reticulo rumen of the animal an article according to claim 20.

27. A method of remedying an element deficiency in a ruminant animal comprising lodging in the reticulo rumen of the animal an article according to claim 21.

* * * * *